United States Patent
Toumazou et al.

(10) Patent No.: US 10,582,897 B2
(45) Date of Patent: Mar. 10, 2020

(54) METHOD AND DEVICE FOR COMPARING PERSONAL BIOLOGICAL DATA OF TWO USERS

(71) Applicant: DNANudge Limited, London (GB)

(72) Inventors: Christofer Toumazou, London (GB); Georgina Toumazou, London (GB)

(73) Assignee: DNANUDGE LIMITED, London (GB)

(*) Notice: Subject to any disclaimer, the term of this patent is extended or adjusted under 35 U.S.C. 154(b) by 0 days.

(21) Appl. No.: 16/043,709

(22) Filed: Jul. 24, 2018

(65) Prior Publication Data
US 2020/0029908 A1   Jan. 30, 2020

(51) Int. Cl.
| | |
|---|---|
| *G06F 9/54* | (2006.01) |
| *A61B 5/00* | (2006.01) |
| *G06F 3/01* | (2006.01) |
| *G06F 1/16* | (2006.01) |
| *G16H 10/40* | (2018.01) |
| *G16H 10/65* | (2018.01) |
| *A44C 5/00* | (2006.01) |
| *G16B 40/00* | (2019.01) |
| *G06K 7/10* | (2006.01) |

(52) U.S. Cl.
CPC .............. *A61B 5/72* (2013.01); *A44C 5/0015* (2013.01); *A61B 5/0024* (2013.01); *G06F 1/163* (2013.01); *G06F 3/016* (2013.01); *G06F 3/017* (2013.01); *G06F 9/54* (2013.01); *G16B 40/00* (2019.02); *G16H 10/40* (2018.01); *G16H 10/65* (2018.01); *G06K 7/10821* (2013.01)

(58) Field of Classification Search
CPC .... G06F 9/546; G06Q 10/10; H04L 29/08072
USPC .................................. 719/313; 709/204, 217
See application file for complete search history.

(56) References Cited

U.S. PATENT DOCUMENTS

| | | | | |
|---|---|---|---|---|
| 6,711,414 | B1* | 3/2004 | Lightman | G06Q 30/02 340/853.2 |
| 9,013,300 | B2* | 4/2015 | Felix | H04W 4/90 340/539.13 |
| 9,775,015 | B1* | 9/2017 | Mishra | H04W 4/023 |
| 9,858,799 | B1* | 1/2018 | DeLuca | A61B 5/02438 |
| 9,901,301 | B2* | 2/2018 | Brenner | G06F 19/00 |
| 2003/0208110 | A1 | 11/2003 | Mault et al. | |
| 2003/0226695 | A1 | 12/2003 | Mault | |
| 2005/0021679 | A1* | 1/2005 | Lightman | G06Q 30/02 709/219 |

(Continued)

FOREIGN PATENT DOCUMENTS

| | | |
|---|---|---|
| EP | 2416269 A2 | 2/2012 |
| WO | 03/105445 | 12/2003 |
| WO | 2012/135557 | 10/2012 |

(Continued)

*Primary Examiner* — Andy Ho
(74) *Attorney, Agent, or Firm* — Saul Ewing Arnstein & Lehr LLP

(57) ABSTRACT

A wearable device comprising a memory storing data associated with a personal biology of a user, a short-range wireless transceiver for receiving, from a peer wearable device, data associated with a personal biology of a peer user, and a processor for comparing the received data with the data stored in the memory in order to determine whether or not there is a match. The device further comprises an indicator for generating a visual, audio or other sensory indication of a match when the data is determined to match.

15 Claims, 3 Drawing Sheets

(56) References Cited

U.S. PATENT DOCUMENTS

| | | |
|---|---|---|
| 2006/0256074 A1 | 11/2006 | Krum et al. |
| 2008/0208971 A1 | 8/2008 | Costin et al. |
| 2015/0112857 A1* | 4/2015 | Gellis .................... G06Q 50/01 705/39 |
| 2016/0071423 A1 | 3/2016 | Sales et al. |
| 2016/0219124 A1* | 7/2016 | Elgrichi ................ H04L 67/306 |
| 2017/0098268 A1 | 4/2017 | Karvela et al. |
| 2017/0323057 A1 | 11/2017 | Karvela et al. |
| 2018/0053242 A1* | 2/2018 | Agrawal ............ G06K 7/10554 |
| 2018/0140203 A1* | 5/2018 | Wang ................... A61B 5/0205 |
| 2018/0236242 A1* | 8/2018 | Balinski ............. A61N 1/36585 |

FOREIGN PATENT DOCUMENTS

| | | |
|---|---|---|
| WO | 2015/077512 | 5/2015 |

\* cited by examiner

METHOD AND DEVICE FOR COMPARING PERSONAL BIOLOGICAL DATA OF TWO USERS

TECHNICAL FIELD OF THE INVENTION

The present invention relates to a method and wearable device for comparing personal biological data of two users.

BACKGROUND OF THE INVENTION

Semiconductor nanotechnology and optical technologies have made significant contributions to people's lifestyle, especially by facilitating hardware miniaturisation. Its application to the sequencing and genotyping industry has enabled so-called "lab-on-chip" systems. Depending on the biological questions/genes of interest, primer(s)/probe(s)—more generally referred to as "biomarkers"—are designed accordingly. A biomarker is an oligonucleotide such as a DNA molecule and may target certain gene(s)/variation(s). A biomarker may alternatively, for example, be an antibody or an antigen. By applying/choosing different types of biomarkers on such systems, a customer can test his/her biological sample, DNA, RNA, protein etc, (extracted locally or remotely by a third party from e.g. saliva, blood, urine, tissue, stool, hair etc.) for specific traits, possibly as dictated by certain lifestyle concerns or interest.

Such "personal" genetic or biological information enables medical decisions to be made more effectively, for example, by selecting treatments or drug doses which are more likely to work for particular patients. Identifying individual differences at a molecular level also allows lifestyle and dietary advice to be tailored according to the needs of individuals or particular classes of individuals. For example, personal care products such as cosmetics and nutraceuticals may be selected based on how effective these products are for individuals having certain single nucleotide polymorphisms in their DNA. A number of private companies have been created in order to cater for the growing consumer genetics market and every day new genetic traits are being described, generating a continuously expanding catalogue of biomarkers that have the potential to offer insight into the health, wellbeing, and, in the case of genetic variations, phenotype, of a great many people.

Whilst such "unlocking" of an individual's genetic data as described above may benefit the individual in many different ways, the abstract nature of the data may make it difficult for the individual to appreciate its value. For example, individuals may not feel that they have "ownership" of their data or they may feel they are unable themselves to make use of their data because of its complexity or inaccessibility. Privacy concerns may also dissuade individuals from making use of their data.

US2017/0323057A1 describes a wearable device for providing product recommendations based on a user's biological information, such as genetic data. The wearable device incorporates a laser scanner or barcode reader which the wearer of the device uses to identify a product he or she is interested in purchasing or consuming. The device then provides an indication whether or not the product is recommended for the wearer based on his or her biological information. For example, an analysis of a user's DNA may have revealed that the user metabolises caffeine more slowly than most other people, in which case, the wearable device may recommend that he or she avoids coffee. Users of the wearable device described in US2017/0323057A1 are, however, not easily able to compare product recommendations or biological information with one another. Whilst two users may, for example, scan the same product and see whether or not the indication provided by their respective wearable devices is the same, this process can be laborious and does not necessarily allow users to identify which aspects of their biological or genetic identities are different or which aspects they may have in common. Users can of course discuss their biological information while simultaneously viewing the information on their smartphones. Nonetheless, a fast, almost instantaneous, method of comparing information is desirable.

SUMMARY OF THE INVENTION

According to a first aspect of the present invention there is provided a wearable device comprising a memory storing data associated with a personal biology of a user, a short-range wireless transceiver for receiving, from a peer wearable device, data associated with a personal biology of a peer user, and a processor for comparing the received data with the data stored in the memory in order to determine whether or not there is a match. The device further comprises an indicator for generating a visual, audio or other sensory indication of a match when the data is determined to match.

The device may be operable to receive the data from a peer wearable device in response to detecting that the peer wearable device is within a predefined distance or is in contact. The step of detecting that the other wearable device is within a predefined distance of the wearable device may comprise detecting that the strength or quality of a signal transmitted from the peer wearable device exceeds a predefined value. The transceiver may operate using Bluetooth protocol, preferably a Bluetooth Low Energy profile, or a near-field communication protocol. The predefined distance may less than 10 cm, preferably less than 5 cm, or possibly less than 0.5 cm.

The indicator may be configured to generate a visual, audio or other sensory indication of a non-match when the data does not match.

The data associated with a personal biology of a user may comprise one or more scores, the or each score indicating whether the user is predisposed to or has an associated personal behaviour or condition. By way of example, the data may indicate a user's ability to metabolise caffeine, his or her sensitivity to calories and carbohydrates etc, all of which characteristics are derivable from an analysis of certain parts of the user's genetics.

The wearable device is a wrist-worn device, e.g. comprising a wristband or wrist strap.

The transceiver may be configured to transmit the data associated with a personal biology of a user stored in said memory, to the peer device, in response to detecting that the peer device is within a predefined distance or in contact.

The wearable device may comprise a sensor, such as an accelerometer, for detecting a user input or gesture. The device is configured upon detection of such an input or gesture to switch from a first mode in which data is not exchanged with a peer device to a second mode in which data is exchanged.

The device may comprise a memory storing product codes and product code recommendations, and a product code reader for reading a product code from a product. The processor may configured to obtain a product recommendation for a read product code and said indicator is configured to generate a visual, audio or other sensory indication of the obtained product recommendation. The product code reader may be a barcode scanner.

The wearable device may be a smartphone.

According to a second aspect of the present invention there is provided a system for allowing a user to compare data, associated with his or her personal biology, with a peer user. The system comprises a wearable device according to the above first aspect of the invention and a computer device in wireless communication with said wearable device, the computer device allowing the user to select the data on which the match is to be carried out from a set of data stored in the memory of the wearable device. The wearable device may be a wrist-worn device and the computer device may be a smartphone.

According to a third aspect of the present invention there is provided a computer-implemented method of comparing data associated with personal biologies of respective users stored on respective wearable devices. The method comprises detecting by the wearable devices that the wearable devices are within a predefined distance of each other or in contact with each other and, in response to said detection, exchanging said data between the devices via a wireless interface. The method further comprises comparing the data of the users at one or both of the devices to determine whether or not the data matches, and operating an indicator at one or both of the devices to provide a visual, audio or other sensory indication of a match when the data is determined to match.

The method may comprise providing individual selection or deselection control of categories of biological information to be shared with others through external computer devices such as smartphones in communication with said wearable devices.

DETAILED DESCRIPTION OF THE INVENTION

Figure 1:
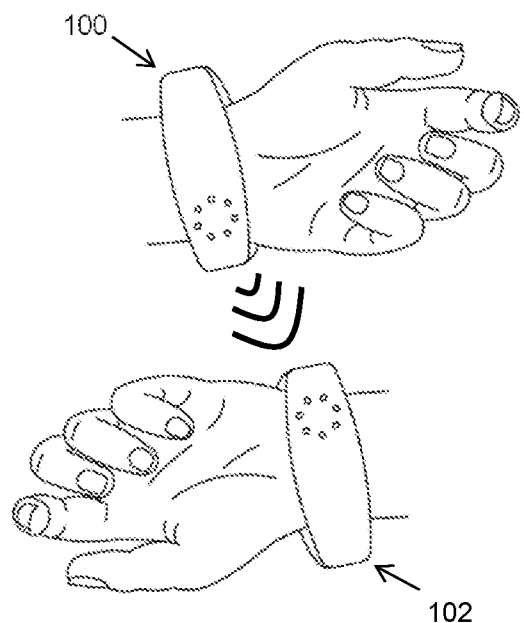
FIG. 1 illustrates schematically a pair of users exchanging personal biological information using wearable devices.

The embodiments described here aim to address the problems described above by allowing users to compare their personal biological information in a way which is convenient and secure. This personal biological data is typically data derived from a person's biology, e.g. genetic traits. The personal biological information is stored on a wearable device which comprises a transmitter and receiver for transferring the biological data from between wearable devices when they are brought close to or in contact with one another. After the biological data has been exchanged, the wearable device compares the two sets of data to determine aspects of the data which are common to both users and/or the differences between the two sets of data. Performing the comparison at the wearable device helps ensure that the process is quick and reliable, e.g. because communication with a remote server is not required. This does not preclude of course the involvement of a remote server (e.g. in the "cloud"). The results of the comparison are then presented to the users. For example, although a pair of friends/users may each know that they themselves have gluten intolerance, they may otherwise be unaware that their friend has the same intolerance. Conversely, one user may have a predisposition which requires them to abstain from eating too much red meat, whereas another user may be predisposed to anaemia, requiring them to eat an iron/meat rich diet. Comparisons based on the biological information of the two users may therefore encourage them discuss how to best manage a particular condition or to decide on a meal they can share or a restaurant which is appropriate for them both.

Allowing users to "share and compare" their biological information with a simple cooperative gesture provides a playful and social dimension to what might otherwise seem to the users to be a fairly abstract exercise. For example, when there is a "match" for the biological information of two users then the social connection between those users may be reinforced, or the process of making the comparison may act as an "icebreaker" for further interactions and discussions between the two users. Furthermore, these social aspects may encourage the users to have a greater awareness of their biological identities and lead or "nudge" them towards making better health and lifestyle decisions.

The personal biological data that is compared is not limited to data relating to nutrition but can extend to any characteristics that are derived from personal biological data. For example, data that is compared may relate to skincare and cosmetics/cosmeceuticals, fitness/activity, smoking, alcohol, etc.

The personal biological information of a user may comprise personal genetic or epigenetic data or proteomic data, obtained by an analysis of a biological sample (e.g. a mouth swab) provided by the user. For example, the biological sample can be analysed using primers, strands of short nucleic acid sequences that serve as a starting point for DNA synthesis. As is known in the prior art, such primers can be used in the detection of genetic single-nucleotide polymorphisms (SNPs) and more particularly to determine the variation type (or allele) of a tested individual for a given SNP. Alternatively, or additionally, the personal biological information may comprise information related to the microbiome of the user, such as the presence or absence of certain gut bacteria (e.g. *Helicobacter pylori*). Such microbiome data may be obtained by breath testing. The personal biological information may also comprise information about a physiological property of the user (such as the current or historic heart rate of the user), which in some cases, may be obtained by a sensing device incorporated in the wearable device.

The personal biological information may also be derived from one or more of the above types of data. For example, the personal biological data may comprise recommendations for certain products or services, or classes of product or services, which an analysis of the above types of data has revealed are particularly suitable for the user or that should be avoided by the user. These recommendations may be derived from biological filter codes which map to respective products or services or categories of products or services but do not explicitly identify a user's genetic or biological information. For example, there may be a biological filter code which indicates that a user is likely to be more adversely affected (because of his or her genetic traits) by foods with high cholesterol. In this case, by comparing the biological filter codes (or the biological information used to derive the filter codes), users are able to be see whether they are likely to be recommended similar products or services. This may encourage greater interaction and discussion between the users and may give rise to a positive "synergy"

in which the users are more likely to take notice of the product recommendations and/or more likely to compare their biological data.

FIG. 1 illustrates two users exchanging personal biological information using wrist-worn wearable devices 100, 102. In the example shown in the figure, the expanding curved lines indicate that information is being transmitted from one device 100 and received by the other device 102. In this case, a Bluetooth Low Energy (BLE) protocol is used to exchange the biological information, although other protocols designed for data transmission over relatively short distances, such as a near-field communication (NFC) protocol may be used. When an NFC protocol is used, the devices are typically required to be brought within about 5 cm of each other in order to establish a communication channel between them. ISP 1507 (NFC & ANT BLE) module based on Nordic Semiconductor nRF52 chip is used and it is integrated with Cortex M4 CPU, flash, RAM memory and optimised antenna. The range at which a "connection" is established may be (user) configurable.

Transmitting the personal biological information over only a short range means that the users are required to bring their devices into relatively close proximity. This re-assures the users that their data will not be intercepted by third-parties (introducing a high degree of privacy) and adds a social element to the process of exchanging the biological information which is similar to shaking hands, for example. In some examples, the wearable devices may be required to come into contact (or be "tapped" one against the other) in order for the exchange of data to take place or to initiate the exchange. The biological information may also be exchanged in encrypted form. For example, biological information may be encrypted using a public key associated with the intended recipient and then decrypted using the corresponding private key stored on the recipient's wearable device. The recipient's wearable device may also store the received biological information for only a short time (e.g. less than 30 s) or no longer than is necessary for performing the comparison.

Figure 2:
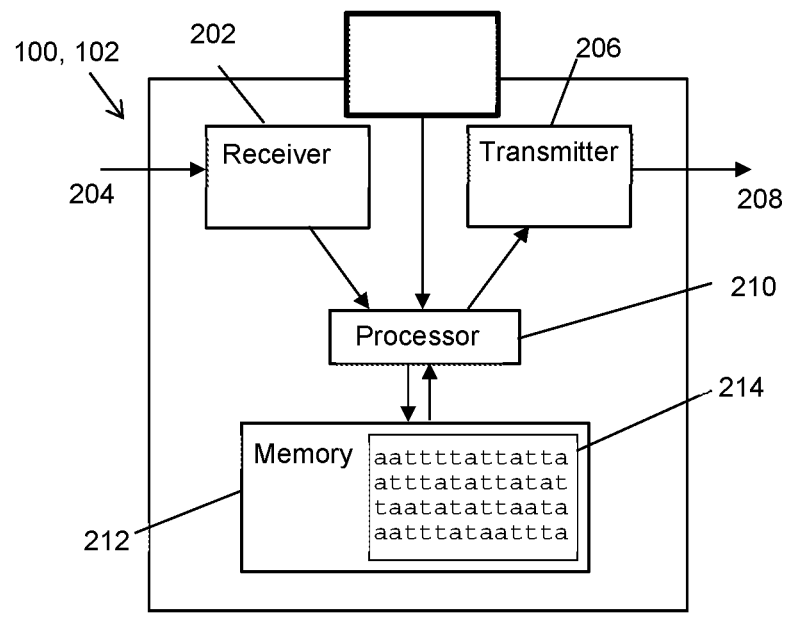
FIG. 2 is a schematic system view of the wearable device of FIG. 1.

FIG. 2 is a schematic system view of the wearable devices 100, 102 of FIG. 1. Each wearable device 100, 102 comprises a gesture sensor for triggering the mode for exchanging data, a receiver 202 for receiving data 204, and a transmitter 206 for transmitting data 208, according to a wireless communication protocol as discussed above. The gesture sensor, the receiver 202 and the transmitter 206 communicate with a processor 210 which is connected to a memory 212 which contains the personal biological information 214 of the user associated with the wearable device 100, 102. In use, the processor 210 retrieves the personal biological information 214 from the memory 212 and transmits it using the transmitter 206. Personal biological information 214 received by receiver 202 can also be stored in memory 212, allowing the processor 210 to compare the received information 214 with the information 214 of the user.

Figure 3:
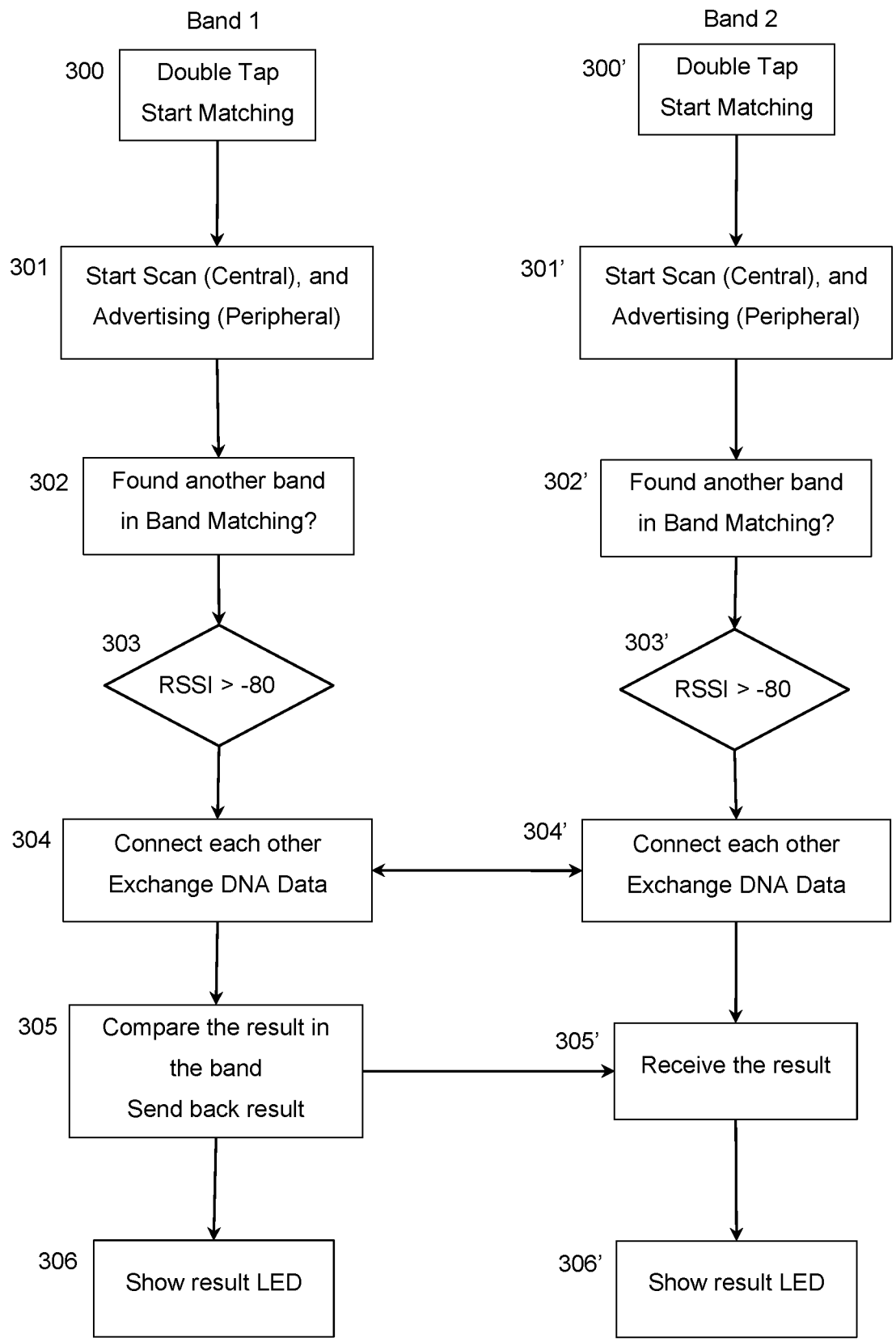
FIG. 3 is a sequence diagram further illustrating how the wearable devices of FIG. 1 can be used to exchange personal biological information.

FIG. 3 is a sequence diagram illustrating how the wearable devices 100, 102 (which are designated in the figure as "Band 1" and "Band 2") can be used to exchange personal biological information. In steps 300 and 300' the respective wearers of the bands perform an action to put the device into a "matching mode". In this example, a "double tap" gesture is used, with the gesture being detected by, for example, an accelerometer/gyroscope (MPU-6050 combining a 3-axis gyroscope and a 3-axis accelerometer) in the wearable device, though of course other gestures or modes of user input, such as a button or a touch screen, can also be used.

Each device may stay in the matching mode for some pre-defined period of time, e.g. 10-15 seconds, after which the matching mode is switched off.

In steps 301 and 301' the devices scan for other devices while simultaneously advertising that they are available for matching. In steps 302 and 302', the respective devices wait until they have found another device in the matching mode. A relative received signal strength indication (RSSI) is measured by each device (steps 303 and 303'). The measured RSSI values are an indication of the power level of the signal being received by each device from the other. Typically, RSSI values may be provided according to a negative scale starting at −100 and ending at 0, with RSSI values closer to 0 indicating stronger received signals. Other scales for measuring the received signal strength can also be used, for example, decibels referenced to one milliwatt (dBm) or a received channel power indicator (RCPI) scale, which is part of the IEEE 802.11 standard. If the RSSI values exceed a certain value (e.g. RSSI>−80 or a received signal strength of −80 dBm), then the devices may connect to each other in order to exchange biological information (steps 304 and 304'). In example shown in the figure, the transfer (exchange) of biological information is unidirectional between the devices.

One of the devices (here, Band 1) receives the personal biological data from Band 2. Band 1 then compares the received biological information with the biological information stored in its memory and then transmits the result(s) of the comparison to the other device (steps 305 and 305') such that both bands now know the result. The comparison of the personal biological information of the users may be carried out in different ways depending on what type of information is exchanged. For example, if the information relates to particular genes, SNPs or DNA sequences, then the comparison may involve determining whether those genes, SNPs or DNA sequences are common to both users. Similarly, if the personal biological information comprises a set of biological filter codes for each user then these sets can be compared to see if there is any overlap. The comparison may also involve determining the probability that the users have a particular characteristic in common in order to provide the users with a measure of how likely or rare it is they share that characteristic.

The results of the comparison may be presented to each user by, for example, illuminating a light-emitting diode (LED) (steps 306 and 306'), e.g. a green colour for the LED may indicate that there is a match between the two users' biological information, whilst a red colour may indicate no match. Other means for presenting the results of the comparison to the users may also be used, such as a display, a haptic device to apply a force or vibration to the wearer of the band, or an audible alarm or voice synthesizer. In an embodiment, each band stores the result temporarily in its RAM memory whilst displaying the result. After the elapse of some short period of time, e.g. 10 seconds, the indication is turned off and the result deleted from the memories of both bands.

Figure 4:
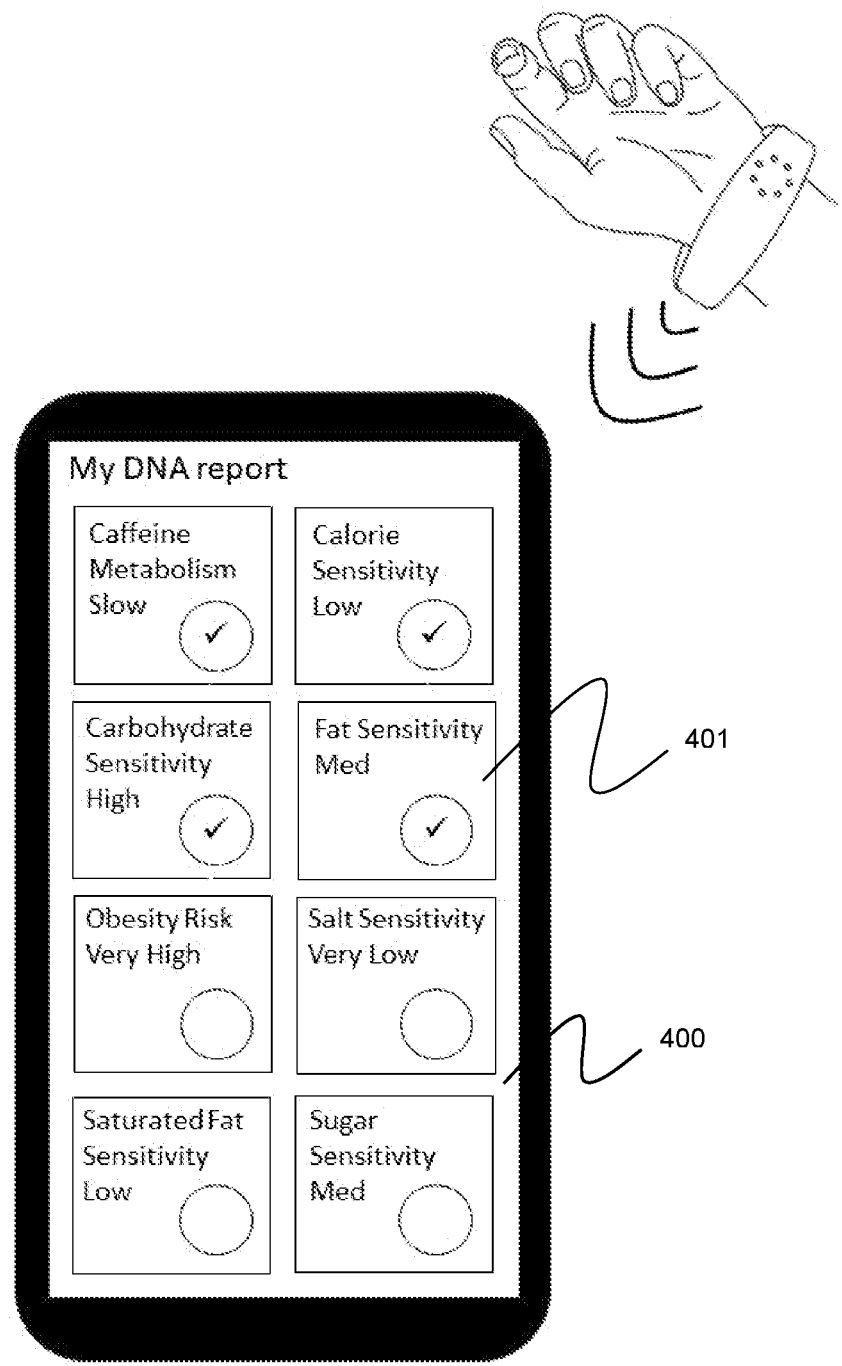
FIG. 4 is a schematic diagram illustrating a user interface for displaying a user's biological information.

The wearable device is likely to have limited means for accepting user inputs. The device may therefore be able to communicate with an external computer device such as a smartphone, e.g. using a Bluetooth interface. The smartphone may be configured with an app that allows the user to control settings on the wearable device. FIG. 4 illustrates a graphical user interface 400 that is provided on a smartphone display, via an installed app, for displaying information associated with a user's personal biological information. In this example, the personal biological information comprises numerical scores for categories such "Calorie sensitivity" or "Fat sensitivity". The numerical scores are mapped to user friendly text descriptions such as "Very High", "High", "Med", "Low" or "Slow" for presentation in the user interface. The different categories are presented as graphical user elements 401. In some implementations, the user may select or deselect the graphical user elements individually in order to control whether the biological information associated with that category should be shared with other users and/or used when comparing the users' biological information. In FIG. 4 for example, the user has selected four panels for sharing, namely "Caffeine Metabolism", "Calorie Sensitivity", "Carbohydrate Sensitivity", and "Fat Sensitivity (shown with selection in the Figure). Such control may be useful for users to avoid revealing, either directly or indirectly, information which they would rather remain private. Comparison of two users' biological information may comprise comparing the numerical scores in each of the categories to determine whether or not any of the scores either match or are approximately the same, i.e. differ by only a small relative or absolute amount. Alternatively, weighted differences of the scores can be used to define a similarity metric indicating how "alike" the users are.

In the case that two peer users have selected categories for matching that are different, this may be indicated by illuminating a third colour of LED, e.g. white, in order to indicate to the users that no matching is possible and that they should consider selecting different categories.

The wearable device may also report back the results of comparisons to the user's smartphone. If the identity of a peer user is known, this could allow results to be logged at the smartphone/app. Based on the results of a comparison, users might then be able to share via their smartphone information regarding purchased products, fitness, etc. In other words, the ability to compare biological related information can form a basis of many different social networking opportunities.

Although not described here in detail, it is possible that bands may be provided with product code readers to allow the bands to read product codes from products being considered for purchase or consumption. Such readers may be barcode scanners and may allow users to obtain product recommendations based upon product data stored in the bands.

It will be appreciated by the person of skill in the art that various modifications may be made to the above described embodiments without departing from the scope of the present invention. It is of course possible that only one of two peer users may have a band, with the other only having a smartphone. In this case, there may be an option in the smartphone app to display a code such as a barcode on the phone's GUI which identifies the user's personal biological data. A peer user having a band can then scan that code using the band's product code reader and perform the comparison described above. Of course, in this case the result may only be displayed on the band, but that may be adequate as both users can see the result.

It will be further appreciated that the invention may be implemented using a pair of smartphones without the need for bands, assuming that both phones are provided with suitable short-range wireless transceivers.

It will also be appreciated that various means may be implemented to place a band in a read-to-match state. For example, a band may switch to this mode when a double tap with another band is detected.

The invention claimed is:

1. A wrist-worn wearable device comprising:
   a memory storing data indicative of a wearer's nutrition and/or skin-related genetic traits and obtained by an analysis of a biological sample provided by the wearer;
   a short-range wireless transceiver for transmitting said data to a peer wrist-worn wearable device and for receiving, from the peer wearable device, corresponding data for the wearer of the peer device, the range of said transceiver being 10 cm or less;
   a processor for comparing received data with the data stored in the memory in order to determine whether or not there is a match between the wearer's and the peer wearer's nutrition and/or skin-related genetic traits; and
   an indicator for generating a visual, audio or other sensory indication of the result.

2. A wrist-worn wearable device according to claim 1 and being operable to receive the data from a peer wearable device in response to detecting that the peer wearable device is within a predefined distance or is in contact.

3. A wrist-worn wearable device according to claim 2, wherein detecting that the other wearable device is within a predefined distance of the wearable device comprises detecting that the strength or quality of a signal transmitted from the peer wearable device exceeds a predefined value.

4. A wrist-worn wearable device according to claim 2, wherein said transceiver operates using Bluetooth protocol, preferably a Bluetooth Low Energy profile, or a near-field communication protocol.

5. A wrist-worn wearable device according to claim 1, wherein said indicator is configured to generate a visual, audio or other sensory indication of a non-match when the data does not match.

6. A wrist-worn wearable device according to claim 1, wherein said data indicative of a wearer's nutrition and/or skin-related genetic traits comprises one or more scores, the or each score indicating whether the user is predisposed to or has an associated personal behaviour or condition.

7. A wrist-worn wearable device according to claim 1 and comprising a wristband or wrist strap.

8. A wrist-worn wearable device according to claim 1 wherein said transceiver is configured to transmit the data indicative of a wearer's nutrition and/or skin-related genetic traits stored in said memory, to the peer device, in response to detecting that the peer device is within a predefined distance or in contact.

9. A wrist-worn wearable device according to claim 1, further comprising an accelerometer for detecting a user input or gesture, the device being configured upon detection of such an input or gesture to switch from a first mode in which data is not exchanged with a peer device to a second mode in which date is exchanged.

10. A wrist-worn wearable device according to claim 1, the wearable device being a smartphone.

11. A system for allowing a user to compare data, associated with his or her personal biology, with a peer user and comprising:
   A wrist-worn wearable device according to claim 1; and
   a computer device in wireless communication with said wearable device, the computer device allowing the user to select the data on which the match is to be carried out from a set of data stored in the memory of the wearable device.

12. A system according to claim 11, wherein said wearable device is a wrist-worn device and said computer device is a smartphone.

13. A computer-implemented method of comparing data indicative of nutrition and/or skin-related genetic traits of respective users stored on respective wearable devices according to claim 1, the method comprising:
- at each of the wearable devices, in response to receiving or detecting a user input or gesture using a button or sensor, switching the wearable device from said first mode to said second mode;
- detecting by the wearable devices that the wearable devices are within a range of each other;
- in response to said detection, exchanging said data between the devices via said short-range transceivers;
- comparing the data of the users at one or both of the devices to determine whether there is a match between the wearers' nutrition and/or skin-related genetic traits; and
- operating an indicator at one or both of the devices to provide a visual, audio or other sensory indication of the result.

14. A computer-implemented method according to claim 13 and comprising providing individual selection or deselection control of categories of biological information to be shared with others through external computer devices such as smartphones in communication with said wearable devices.

15. The wrist-worn wearable device according to claim 1, further comprising a sensor or button for receiving or detecting a user input or gesture, the device being configured upon detection of such an input or gesture to switch from a first mode in which data cannot be exchanged with a peer device using said short-range wireless transceiver to a second mode in which the data can be exchanged if the devices are within range.

* * * * *